United States Patent [19]

Troutner

[11] Patent Number: 4,596,550
[45] Date of Patent: * Jun. 24, 1986

[54] METHOD AND APPARATUS FOR ULTRAFILTRATION MEASUREMENT IN A TWO PUMP DIALYSIS SYSTEM

[75] Inventor: Vernon H. Troutner, St. Petersburg, Fla.

[73] Assignee: Baxter Travenol Laboratories, Inc., Deerfield, Ill.

[*] Notice: The portion of the term of this patent subsequent to Dec. 25, 2001 has been disclaimed.

[21] Appl. No.: 574,791

[22] Filed: Jan. 27, 1984

Related U.S. Application Data

[63] Continuation-in-part of Ser. No. 423,378, Sep. 24, 1982, Pat. No. 4,490,134.

[51] Int. Cl.$^4$ ............................................... A61M 1/03
[52] U.S. Cl. ............................. 604/5; 128/DIG. 13
[58] Field of Search ............... 604/4, 5, 6, 27–31, 604/34, 51, 66–67, 153, 118; 128/DIG. 13; 210/321.2, 321.3

[56] References Cited

U.S. PATENT DOCUMENTS

| | | | |
|---|---|---|---|
| 3,756,234 | 9/1973 | Kopp | 128/214 R |
| 3,830,234 | 8/1974 | Kopp | 128/214 R |
| 3,848,592 | 11/1974 | Willock | 128/214 R |
| 3,902,490 | 9/1975 | Jacobsen et al. | 604/5 X |
| 3,985,134 | 10/1976 | Lissot et al. | 128/214 R |
| 4,231,366 | 11/1980 | Schael | 128/214 T |
| 4,401,431 | 8/1983 | Arp | 604/5 |

*Primary Examiner*—Edward M. Coven
*Attorney, Agent, or Firm*—Paul C. Flattery; Mark A. Hofer; Kay H. Pierce

[57] ABSTRACT

A blood flow system for processing blood has two phases of operation, an arterial phase and a venous phase. During the arterial phase, the system is filled with blood through operation of an arterial blood pump. When a predetermined blood pressure level in the system has been attained, the arterial blood pump is inactivated and a venous blood pump removes blood from the system for a given number of pump turns. By accurately monitoring both arterial and venous pumps operating cycles, ultrafiltration volume and rate may be determined.

13 Claims, 5 Drawing Figures

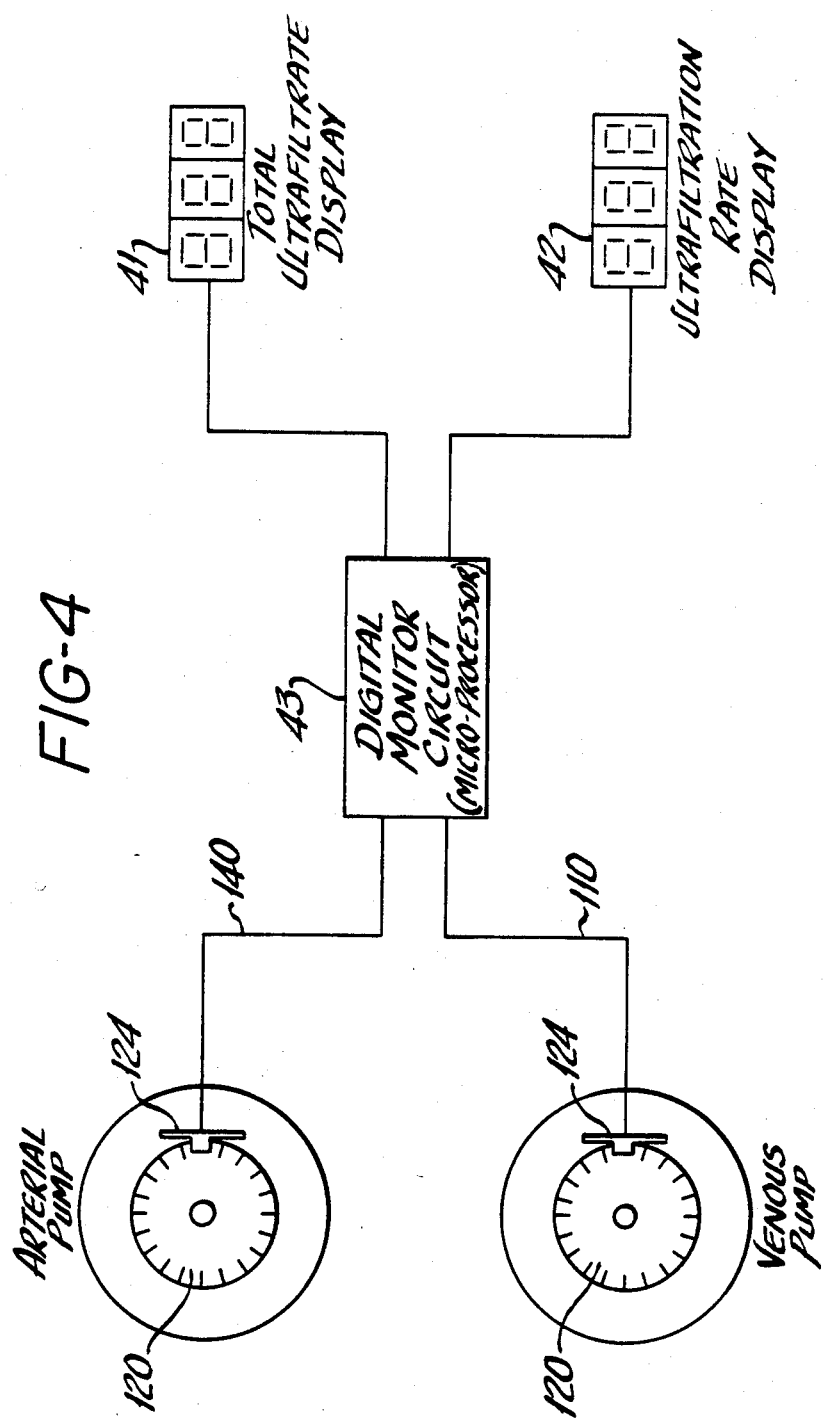

METHOD AND APPARATUS FOR ULTRAFILTRATION MEASUREMENT IN A TWO PUMP DIALYSIS SYSTEM

This application is a continuation-in-part of copending, commonly assigned, application Ser. No. 423,378 filed Sept. 24, 1982 entitled "Dual Phase Blood Flow System and Method of Operation", now U.S. Pat. No. 4,790,134.

The present invention relates to dual phase blood flow systems and, in particular, to dual phase blood flow systems in which ultrafiltration measurements may be accomplished through monitoring arterial and venous pump cycles.

Hemodialysis blood flow systems are employed as a therapeutic measure when a patient's kidneys no longer perform their blood purifying function by reason of disease, removal or other malfunction. Kidney failure results in the accumulation of toxic wastes in the patient's blood. Unless measures are taken to remove these wastes, the patient will experience potentially fatal uremic poisoning. Uremic poisoning may be prevented through the use of hemodialysis, by which blood is drawn from the patient and circulated through a dialyzer. In the dialyzer, the blood is separated from a specially treated dialysate fluid by a membrane which has pores of microscopic size through which waste products from the blood may pass. The microscopic pores are too small, however, to permit the passage of blood cells, proteins, and other essential elements of the blood through the membrane. The waste products thus diffuse into the dialysate fluid and are removed from the patient's blood. The purified blood is then returned to the patient's body.

Recent advances have led to the development of single needle hemodialysis systems, in which blood is extracted from and returned to the patient's body through a single needle with a Y-shaped junction. The patient is generally prepared for hemodialysis by the surgical implantation of an arteriovenous fistula, which joins an artery with a nearby vein. The diversion of arterial blood into the vein causes the vein to become enlarged, permitting relatively easy insertion of the single needle into the arterialized vein, through which an adequate blood flow for hemodialysis is developed. It has been found that fistula vessels are less traumatized by the single needle technique, and that patients benefit psychologically from the reduced number of venipunctures.

In a typical single needle hemodialysis system, blood is alternately cycled from and to the patient's circulatory system by a single blood pump, or by arterial and venous blood pumps, respectively. During the first, or arterial, phase of operation, blood is drawn from the patient and pumped into the dialysis system by the arterial blood pump. Blood is prevented from returning to the needle by the closure of a valve located between the outlet of the arterial pump and the needle, or through clamping action of the venous blood pump. Blood pressure within the system builds until a time at which the arterial pump is turned off, the valve is opened, or the venous pump in a two-pump system is turned on to pump the blood out of the dialysis system and back to the fistula. During this second, or venous, phase of operation, the pressure of the blood in the dialysis system drops substantially. Eventually a point is reached at which the venous pump is turned off, and the cycle repeats.

The cyclical changeover between the arterial and venous pumping phases of operation may be controlled by monitors which provide indications of pressure and-/or time. For instance, the arterial pump may be activated until a monitor indicates that blood pressure at the outlet of the pump has attained a given high pressure threshold level. At that point, the venous pump is activated to return blood to the patient until a given low pressure threshold is reached. The system then cycles between the low and high pressure threshold levels. However, in pressure/pressure systems of the prior art, there is no direct monitoring of the volume of blood that is transported by the two pumps. Instead, the two pumps generally employ pump turn counters, which are monitored to ensure that the turns of each pump, and hence the amount of blood pumped, are equal during each cycle of operation. If the observed turns of one pump turn counter become too high or too low, one or both of the pressure thresholds at which the phase changeovers occur are adjusted to bring the turns counts back into equilibrium. It is possible in such a system for widely varying pressure thresholds to be necessary in order to develop equal pump turns counts of the proper magnitude. This is particularly likely when the capillaries in a capillary-type dialyzer become plugged. Such a condition can cause a change in the volume of blood transported without a change in pressure thresholds.

Alternatively, the two operating phases may be alternated as a function of time. The arterial phase, for example, may be continued for a first predetermined time period. Thereafter, the venous phase may be extended for a second, predetermined time period. When the two phases are properly timed, a steady inflow and outflow of blood may be maintained. However, the time monitoring system can result in the attainment of undesirable blood pressure levels if the capacities of the pumps are either not accurately known or become unstable with use.

Neither of these systems allow for practical measurement of ultrafiltration rates, i.e., the measurement of flow into the dialysate within the dialyzer.

In accordance with the principles of the present invention, a dual phase blood flow system is provided in which the ultrafilatration rates may be determined by monitoring the arterial and venous phases of pump operation in a simple and reliable manner. In the dual phase blood flow system contemplated, a first, arterial pump is activated during the arterial phase to pump blood from the patient and into a blood processor. The arterial pump continues to operate until a pressure monitor indicates that blood pressure at the output of the arterial pump has attained a given threshold level. Upon attainment of the threshold level, a pump control system terminates the arterial phase and initiates a venous phase by activating a second, venous pump. The venous pump is activated for a given number of pump cycles. Since each pump cycle corresponds to the transmission of a given volume of blood, a predetermined amount of blood is pumped out of the blood precessor, through the needle and back to the patient's system during the venous phase of operation.

After the venous pump has been activated for the prescribed number of cycles, the venous phase is terminated and the arterial phase resumes under control of the pump control system. This system requires only a single pressure monitor for control of the arterial phase to assure that undesirably high blood pressures will not be produced in the system. The system also provides a simple control technique for the venous phase to assure that a desired amount of blood is taken from and returned to the patient's circulatory system during each cycle of operation. The control method is direct in that it eliminates the need to adjust pressures to produce the proper number of pump turns per phase.

The arterial pump cycle of operation also corresponds to a given volume of blood. By monitoring both the arterial pump operation and the venous pump operation, and in particular the number of revolutions each pump turns, the ultrafiltration rate through the dialysis membrane in the dialyzer may be determined.

In the drawings:

FIG. 4 illustrates the monitoring relationship of the microprocessor and the arterial and venous pumps.

Figure 1:
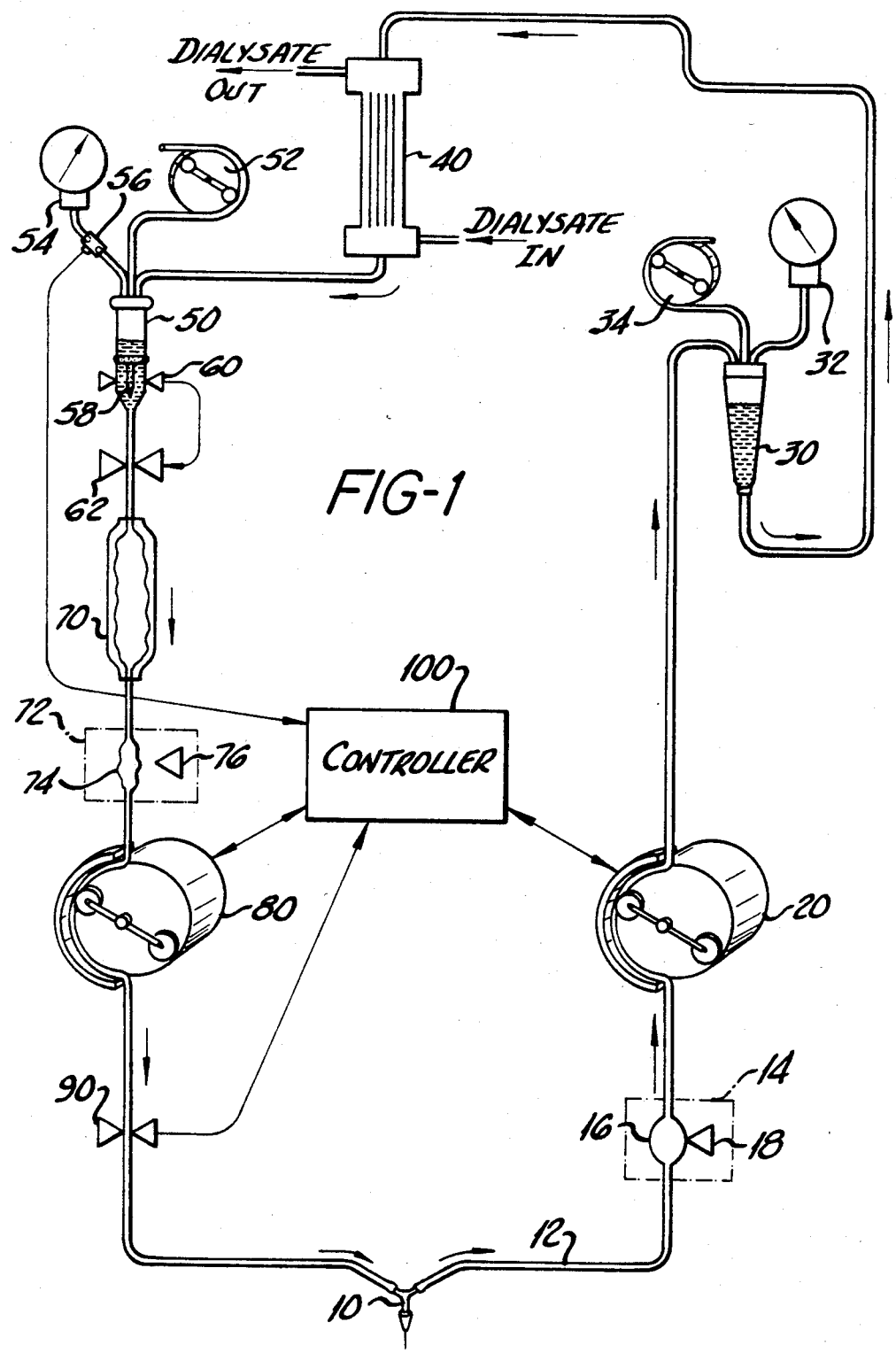
FIG. 1 illustrates the blood circulation path of a single needle hemodialysis system constructed in accordance with the principles of the present invention.

Referring to FIG. 1, the blood flow path of a single needle hemodialysis system is shown, including a single needle 10 suitable for the transfer of blood from and to a patient. In FIG. 1, the arrows indicate the direction of the flow of blood through the system.

From the single needle 10, blood flows through the blood tubing 12 to a negative pressure pillow switch 14. The pillow switch 14 includes a pillow-like section of tubing 16 and a sensor or switch 18 which is responsive to a relaxation of pressure in the pillow-like section 16. When the pillow pressure declines below a certain level the sensor or switch responds by initiating a system alarm as well as other procedures which interrupt the operation of the system.

From the pillow switch 14 the blood tubing is connected through an arterial roller blood pump 20. The arterial blood pump 20 operates under control of a controller 100, as will be described subsequently. The blood tubing is then connected to a post-pump arterial drip chamber 30 which collects blood and accommodates the connection of various gauges to the system. The pressure in the drip chamber 30 is monitored by an arterial mechanical gauge 32 with alarm contacts. The blood level within the chamber 30 may be varied through the operation of a blood level adjust roller pump 34, by which air may be added to or subtracted from the chamber. The outlet of the drip chamber 30 is connected by blood tubing to the inlet of a capillary dialyzer 40. In the dialyzer, impurities in the blood pass through the dialyzer membrane and into dialysate fluid, which flows into and out of the dialyzer through separate ports under control of a dialysate preparation system (not shown).

Purified blood flows out of the dialyzer 40 and into a venous drip chamber 50. The pressure within the venous drip chamber 50 is monitored by a mechanical venous pressure gauge 54 with alarm contacts. A second blood level adjust pump 52 is connected to the drip chamber 50 to add or subtract air from the chamber, thereby adjusting the blood level within the chamber. In a tubing line between the venous drip chamber 50 and the venous pressure gauge 54 is a solid state pressure transducer 56 which controls the cycling of the blood pumps and also provides another monitor of venous blood pressure. The venous drip chamber 50 further includes a filter 58 located within the chamber.

An air/foam detector 60 is located next to the venous drip chamber 50. The detector 60 ultrasonically or optically detects the presence of an abnormal amount of air or foam in the blood and also monitors the blood level in the chamber 50. The detector responds to the occurrence of such an abnormality by activating a clamp 62, which clamps the blood tubing closed to prevent the pumping of foam and air bubbles into the patient's circulatory system.

The blood tubing is then connected to the inlet of a flexible vinyl accumulator bag 70. The outlet of the accumulator bag 70 is coupled to a positive pressure pillow switch 72, which may be merely an extension of the accumulator bag 70 or, as shown in FIG. 1, may include its own pillow-shaped tubing section 74. Abnormal expansion of the pillow-shaped section 74 in response to an undesirable buildup of blood pressure causes the sensor or switch portion 76 to set off an alarm and to interrupt system operation.

From the pillow switch 72 the blood tubing passes through a venous roller blood pump 80 which is operated under control of the controller 100. The blood tubing then passes through a second air/foam detector 90, which is connected into the system alarm by the controller 100. Finally, the blood tubing is connected to the needle 10 to return the purified blood to the patient's circulatory system. The arrangement of FIG. 1 is described in detail in concurrently filed U.S. patent application Ser. No. 423,380 (ECP-72), entitled "Single Needle Alternating Blood Flow System".

Figure 2:
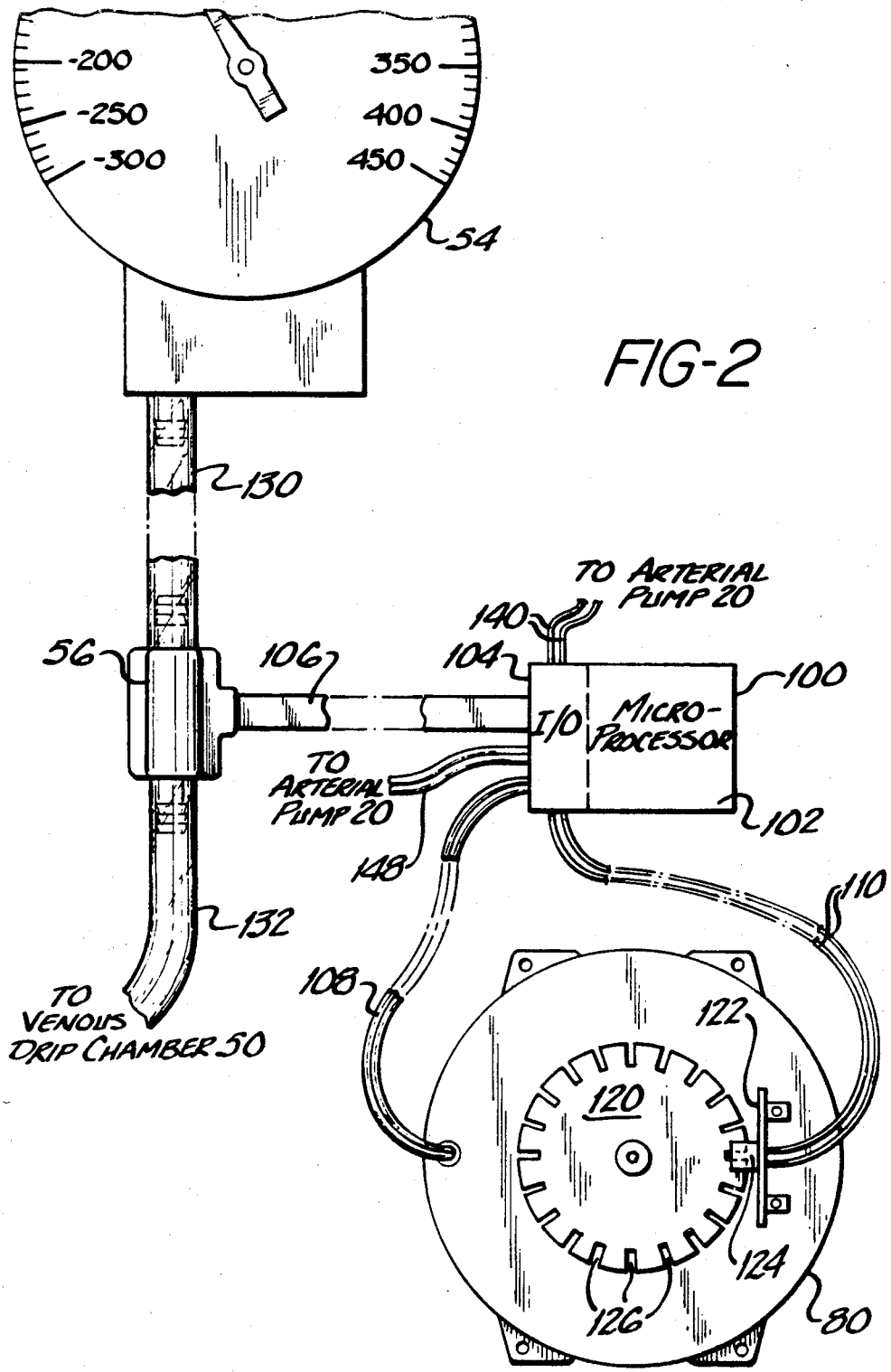
FIG. 2 illustrates in greater detail the control system for the venous and arterial blood pumps of the arrangement of FIG. 1.

The control system for the blood pumps is shown in further detail in FIG. 2. The venous pressure gauge 54 is coupled by way of a tubing section 130 to one port of a solid state flow-through pressure transducer 56. The other port of the pressure transducer 56 is connected to the venous drip chamber 50 by a tubing section 132. The flow-through pressure transducer 56 may be of the type containing an open-ended tube located between the two ports. A silicon chip sensing element is bonded to the side of the tube, and contains a sensing diaphragm and piezoresistors. As the pressure within the tube changes, the diaphragm flexes changing the resistance of the piezoresistors and resulting in an output voltage proportional to pressure. This output voltage is communicated to input/output (I/O) section 104 of controller 100 by way of a cable 106, which in turn applies the information to the microprocessor section 102 of the controller.

The I/0 section 104 of the controller is coupled to the motor of arterial pump 20 by a power cable 148 and to the motor of venous pump 80 by a power cable 108. A power transistor, such as a Darlington transistor switch, may be employed in the I/0 section to switch motor current. The I/0 section is also connected to the arterial and venous pumps by wires 140 and 110, respectively. The wires 140 and 110 convey motor speed information to the controller from slot encoders, with the venous pump slot encoder being shown in FIG. 2. The arterial pump is similarly equipped with a slot encoder. The slot encoder includes a slotted disc 120 mounted on the shaft of the pump motor, an optical detector 124 and a circuit board 122. As the disc 120 turns on the motor shaft, the slots 126 along the perimeter of the disc are sensed by optical detector 124 and are indicated by pulses produced by circuitry on circuit board 122. The pulses are applied to the controller 100 by way of wires 110 and 140, thereby providing the microprocessor with an indication of the motor speed of the venous pump and arterial pump respectively. The slot encoder for the arterial pump operates in a similar manner.

In operation, the arterial blood pump 20 of FIG. 1 is activated by the controller 100 to begin withdrawing blood from the patient through the needle 10. The negative pressure pillow switch safeguards against the withdrawal of blood at too great a rate, as indicated by the development of a negative pressure at the switch. Withdrawal of blood at too great a rate by the arterial pump can lead to occlusion of the patient's fistula, blood foaming or recirculation of purified blood at the needle junction. The pillow switch also guards against any blockage of blood flow in the fistula and needle; a condition which activates a system shutdown.

Figure 3A:
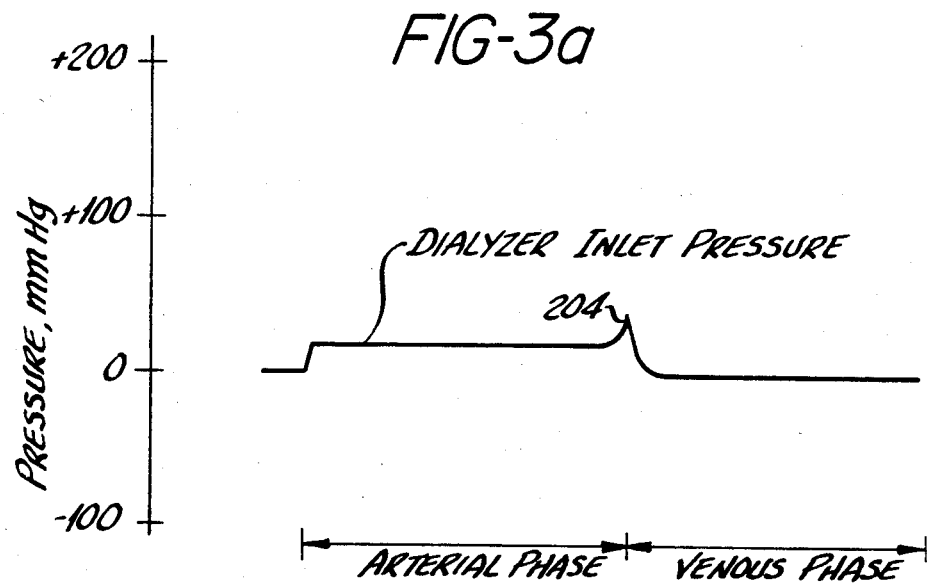
FIGS. 3a and 3b graphically represent phases of operation of the arrangement of FIGS. 1 and 2.

The patient's blood is pumped through the blood tubing 12, the arterial drip chamber 30, and into the dialyzer 40. The flow of blood is virtually unimpeded up to the dialyzer, at which point the pressure developed by the arterial pump forces the blood through the capillaries of the dialyzer. The dialyzer constitutes the only significant pressure drop between the arterial blood pump 20 and the accumulator bag. This pressure drop will vary with the type of dialyzer. FIG. 3a illustrates the typical inlet pressure of a capillary-type dialyzer. During the arterial phase of operation, when the arterial blood pump 20 is running, the dialyzer inlet pressure in this example is seen to remain substantially at 20 to 25 mm Hg relative to atmospheric pressure, which would be indicated on the arterial gauge 32.

Figure 3B:
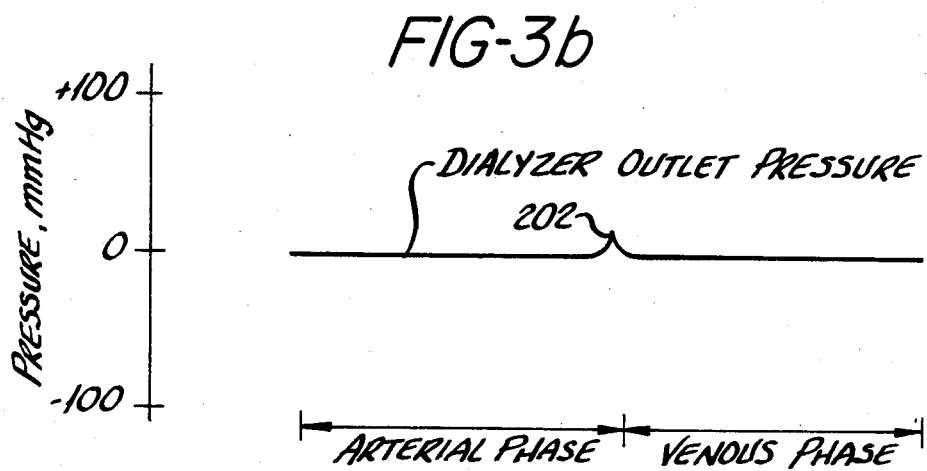

At the outlet of the dialyzer, however, blood pressure remains substantially at 0 mm Hg (gage), as shown in FIG. 3b. This is because the purified blood is free to flow into the venous drip chamber 50, and then into the accumulator bag 70. The accumulator bag is initially empty, and easily fills with blood from the drip chamber, since the outside of the bag is referenced to atmospheric pressure. Thus, as the accumulator bag fills, it produces substantially no back pressure which would impede the flow of blood out of the dialyzer. Furthermore, since the accumulator bag is referenced to atmospheric pressure, the pressure sensing devices at the outlet side of the dialyzer, such as the venous pressure gage 54 and the pressure transducer 56, can indicate the accumulator bag pressure directly by being similarly referenced to atmospheric pressure.

The accumulator bag fills freely with blood until full, which may typically be a capacity of 70 ml., at which time its expansive limits are approached and the pressure in the accumulator bag and venous drip chamber begins to rise, as indicated at 202 in FIG. 3b. This rise in pressure is translated back to the inlet side of the dialyzer, as shown at 204 in FIG. 3a. The relatively small rise in pressure (as compared to the operating pressures of conventional pressure/pressure systems) is indicated by both the arterial and venous mechanical gages 32 and 54, and is also sensed by the solid state pressure transducer 56. The electrical signal produced by the transducer 56 on cable 106 begins to change, and the changing value is applied to the microprocessor 102. The microprocessor responds to the attainment of a voltage indicative of a predetermined pressure in the venous drip chamber by stopping operation of the arterial blood pump 20 in FIG. 1 and initiating operation of the venous blood pump 80. In the example of FIG. 3b, the dialyzer outlet pressure at which the arterial pump is turned off is seen to be approximately 20 mm Hg. The positive pressure pillow switch 72 guards against the attainment of an unusually high venous pressure by shutting down the system if such pressures are approached.

When the venous blood pump 80 is activated, purified blood is withdrawn from the accumulator bag and returned to the patient's system. As the pump operates, the pump motor rotates the slotted disc 120, thereby causing the optical detector 124 to send a series of pulses to the microprocessor 102. The disc will generally rotate faster than the pump rollers turn by virtue of a system of gears. For instance, the pump may be geared so that the slotted disc 120 will rotate 49 times for each turn of the pump rollers. Thus, when the disc contains 20 slots as shown in FIG. 2, 980 pulses will be produced during one rotation of the pump rollers. By counting the pulses, the controller can accurately determine how many turns or fractions of a turn the pump rollers have completed and, by knowing the size of the blood tubing segment used in the pump, the volume of blood moved by the pump can be precisely known. In the present example, it is desired to withdraw 40 ml. of blood from the accumulator bag and to return it to the patient. Assuming that one pump revolution corresponds to the transfer of 16 ml. of blood, it is seen that $2\frac{1}{2}$ pump turns are required to pump 40 ml. of blood. Two and one-half pump turns are indicated by 2450 pulses of the slot encoder. Therefore, the venous blood pump 80 will run until the controller 100 has counted 2450 pulses from its encoder, at which time the pump is stopped, the venous phase is terminated, and a new arterial phase begins.

Similarly, the arterial pump turns are monitored by the controller-microprocessor so that the number of turns required to fill the flexible accumulator bag can be counted. Since the blood volume output of the arterial pump per turn is known, the volume of blood pumped by the arterial pump can be readily calculated by the microprocessor. Since the fluid volume pumped in during the arterial phase must exactly equal the fluid pumped out during the venous phase, the latter being a known quantity, in order to maintain approximately 0 gauge (atmospheric) pressure, any differences in volume pumped by the arterial pump in order to fill the flexible accumulator bag as compared to volume pumped out by the venous pump must be attributable to losses due to ultrafiltration. In other words, to make up for the fluid loss due to ultrafiltration during proper operation of the dialyzer, the arterial pump must pump more to fill the accumulator. By subtracting the venous pump volume after each complete venous-arterial cycle, and accumulating this difference, the total accumulated volume of ultrafiltration can be obtained and if desired, displayed 41, FIG. 3. Similarly, the mean ultrafiltration rate, a volume per time measurement may then be easily calculated by the controller 43 (i.e., dividing the ultrafiltration volume by the time elapsed) and displayed by an appropriate display 42. As may be readily appreciated, the precision of the rate determination improves with an increasing number of venous-arterial cycles.

Returning now to the operation, as blood is returned to the patient the venous pressure at the outlet of the dialyzer rapidly falls back to zero mm Hg gage, as shown in FIG. 3b, as the accumulator bag quickly relaxes. At the same time, the blood pressure at the inlet side of the dialyzer drops back toward zero gage pressure since the arterial blood pump is turned off. This means that blood flow through the dialyzer occurs primarily during the arterial phase of the system, when the arterial blood pump is forcing blood through the dialyzer. Since the dialyzer pressure does not go below zero as the accumulator bag is emptied, undesirable negative transmembrane pressures are not produced in the system. While the blood is being returned to the patient during the venous phase, the air/foam detector 90 monitors the returning blood and alerts the controller 100 if an undesirable amount of air or foam is contained in the blood.

During succeeding arterial phases, the arterial blood pump 20 will fill the accumulator bag 70 after the pumping of only 40 ml. of blood, since the venous blood pump withdraws only 40 ml. of blood from the bag during each venous phase of operation. Thus, the two pumps will alternately transfer 40 ml. of blood into and out of the hemodialysis system, with the arterial phase being ended as a function of blood pressure, and the venous phase being ended as a function of pump turns corresponding to blood volume.

Since in practice, the volume per turn for each pump may not be exactly equal due to manufacturing tolerances, it will be desirable to calibrate the system. This may be readily accomplished by shunting the blood lines which normally connect the dialyzer while recirculating a primary fluid such a saline. During this operation, there is zero ultrafiltration and consequently, any difference between the venous pump pulses and arterial pump pulses after a given number of complete venous-arterial cycles can be used by the microprocessor-controller to generate a correction factor.

I claim:

1. In a dual pump blood processing system for a patient wherein an arterial pump fills blood processing means with blood from the patient and a venous pump removes a known volume of blood from said blood processing means between said arterial and venous pumps and returns said blood to the patient, said arterial and venous pumps being alternately operated to fill and remove blood in response to control means, apparatus for performing ultrafiltration measurements comprising:
   (a) first means associated with said arterial pump for providing first signals responsive to the volume pumped by said arterial pump;
   (b) second means associated with said venous pump for providing second signals responsive to the volume pumped by said venous pump;
   (c) first and second signal connecting means for communicating said first and second signals to said control means and wherein said control means calculates the ultrafiltration volume in response to said first and second signals.

2. The apparatus as set forth in claim 1 wherein said control means further calculates the ultrafiltration rate based on the ultrafiltration volume and the elapsed time.

3. The apparatus as set forth in claim 1 wherein said first and second means comprises a slot encoder and said control means comprises a microprocessor with display means.

4. A low pressure blood processing system for a patient comprising:
   means for withdrawing blood from said patient;
   a first arterial blood pump having an input coupled to said withdrawing means and an output at which a flow of blood is provided when said pump is activated;
   means for processing blood having an input coupled to the output of said arterial blood pump and an output at which a flow of processed blood is produced;
   a second venous blood pump having an input coupled to the output of said blood processing system, and an output;
   means, coupled to the output of said venous blood pump, for returning processed blood to said patient, wherein said blood processing system exhibits a given blood capacity when full;
   a monitor coupled to said blood processing system for detecting the attainment of said given blood capacity;
   blood pump control means, coupled to said pumps and said monitor, for activating said venous blood pump upon detection of said given blood capacity, and for activating said arterial blood pump after said venous blood pump has been activated for a given number of operating cycles;
   first means associated with said arterial blood pump and connected to said control means for providing to said control means first signals responsive to the volume of blood pumped by said arterial pump;
   second means associated with said venous blood pump and connected to said control means for providing to said control means second signals responsive to the volume of blood pumped by said venous pump; and
   wherein said control means displays ultrafiltration information in response to said first and second signals.

5. A low pressure blood processing system for a patient comprising:
   means for withdrawing blood from said patient;
   a first arterial blood pump having an input coupled to said withdrawing means and an output at which a flow of blood is provided when said pump is activated;
   means for processing blood having an input coupled to the output of said arterial blood pump and an output at which a flow of processed blood is produced;
   a second venous blood pump having an input coupled to the output of said blood processing system, and an output;
   means, coupled to the output of said venous blood pump, for returning processed blood to said patient;
   a pressure monitor coupled to said blood processing system for detecting the blood pressure therein;
   blood pump control means, coupled to said pumps and said monitor, for activating said venous blood pump when said detected blood pressure of said blood processing system attains a given threshold, and for activating said arterial blood pump after said venous blood pump has been activated for a given number of operating cycles;
   first means associated with said arterial blood pump and connected to said control means for providing to said control means first signals responsive to the volume of blood pumped by said arterial pump;
   second means associated with said means blood pump and connected to said control means for providing to said control means second signals responsive to the volume of blood pumped by said venous pump; and wherein said control means displays ultrafiltration information in response to said first and second signals.

6. The blood processing system of claim 4, wherein said processing means comprises a dialyzer for performing hemodialysis, and said system further comprises a flexible blood accumulator coupled between said dialyzer and said second venous blood pump, said accumulator exhibiting a known blood capacity when full, and said first and second means include a slot encoder and said ultrafiltration information includes ultrafiltration volume and ultrafiltration rate.

7. The blood processing system of claim 5, wherein said processing means comprises a dialyzer for performing hemodialysis, and said system further comprises a flexible blood accumulator coupled between said dialyzer and said second venous blood pump, said accumulator exhibiting a known blood capacity when full, and said first and second means include a slot encoder and said ultrafiltration information includes ultrafiltration volume and ultrafiltration rate.

8. The blood processing system of claim 6, wherein said monitor comprises a pressure transducer coupled between said dialyzer and said venous blood pump for measuring venous blood pressure.

9. The blood processing system of claim 7, wherein said monitor comprises a pressure transducer coupled between said dialyzer and said venous blood pump for measuring venous blood pressure.

10. The blood processing system of claim 6, wherein said first and second means detect operating cycles of said arterial and venous blood pumps respectively, and communicate said operating cycle information to said control means which calculates volume of blood pumped by each pump based on each pump's known volume per cycle pumping characteristics.

11. The blood processing system of claim 7, wherein said first and second means detect operating cycles of said arterial and venous blood pumps respectively and communicate said operating cycle information to said control means which calculates volume of blood pumped by each pump based on each pump's known volume per cycle pumping characteristics.

12. A method of determining ultrafiltration volume in a hemodialysis system which includes a dialyzer, an arterial blood pump coupled to pump a known volume of blood per pump operating cycle between a patient and an input of the dialyzer, and a venous blood pump coupled to pump a known volume of blood per pump operating cycle between an output of the dialyzer and the patient, said method comprising the steps of:
   (a) activating said arterial blood pump while said venous pump is inactive until the blood pressure in the system between said blood pumps attains a given relatively low level,
   (b) counting the number of operating cycles performed by said arterial pump during activation;
   (c) activating said venous blood pump while said arterial pump is inactive for a predetermined number of operating cycles; and
   (d) calculating the ultrafiltration volume in response to the number of operating cycles performed by said arterial and venous blood pumps.

13. A method of operating a hemodialysis system which includes a dialyzer, an arterial blood pump coupled to pump blood between a patient and an input of the dialyzer, and a venous blood pump coupled to pump a known volume of blood per pump operating cycle between an output of the dialyzer and the patient, said method comprising the steps of:
   (a) activating said arterial blood pump while said venous pump is inactive and the blood pressure at said output of said dialyzer remains substantially equal to atmospheric pressure and, when said blood pressure at the output of said dialyzer increases a predetermined, relatively small amount, above atmospheric pressure;
   (b) counting the number of turns performed by said arterial pump during activation;
   (c) activating said venous blood pump while said arterial pump is inactive for a predetermined number of pump turns; and
   (d) calculating the ultrafiltration volume in response to the number of turns and fractions thereof of said arterial and venous pumps.

* * * * *